United States Patent
Lee et al.

(10) Patent No.: US 9,273,278 B2
(45) Date of Patent: Mar. 1, 2016

(54) LARGE SCALE CELL HARVESTING METHOD FOR PACK-BED CULTURE DEVICE

(71) Applicant: CESCO BIOENGINEERING CO., LTD., Taichung (TW)

(72) Inventors: Vincent Lee, Taichung (TW); Peter Chen, Taichung (TW); Audrey Chen, Taichung (TW); Alex Liu, Taichung (TW); Chungnan Fu, Taichung (TW); Gray Wang, Taichung (TW); Hugo Chen, Taichung (TW); King-Ming Chang, Hsin-Chu (TW); Lewis Ho, Lawrenceville, GA (US)

(73) Assignee: CESCO BIOENGINEERING CO., LTD., Taichung (TW)

( * ) Notice: Subject to any disclaimer, the term of this patent is extended or adjusted under 35 U.S.C. 154(b) by 0 days.

(21) Appl. No.: 14/148,631

(22) Filed: Jan. 6, 2014

(65) Prior Publication Data

US 2014/0193901 A1    Jul. 10, 2014

Related U.S. Application Data

(60) Provisional application No. 61/749,736, filed on Jan. 7, 2013.

(51) Int. Cl.
*C12N 11/00* (2006.01)
*C12M 1/02* (2006.01)
*C12M 1/12* (2006.01)
*C12M 1/00* (2006.01)

(52) U.S. Cl.
CPC ............... *C12M 25/14* (2013.01); *C12M 47/02* (2013.01)

(58) Field of Classification Search
None
See application file for complete search history.

(56) References Cited

U.S. PATENT DOCUMENTS

2008/0220523 A1 * 9/2008 Antwiler .................... 435/394
2010/0267142 A1 * 10/2010 Wang et al. ................. 435/395

FOREIGN PATENT DOCUMENTS

WO    WO 2012140519 A2 * 10/2012

OTHER PUBLICATIONS

CESCO BioProducts webpage. http://www.cescobioproducts.com/bionoc-ii-microcarriers.html; accessed on May 13, 2015.*

* cited by examiner

*Primary Examiner* — Renee Claytor
*Assistant Examiner* — Michelle F Paguio Frising
(74) *Attorney, Agent, or Firm* — Muncy, Geissler, Olds & Lowe, P.C.

(57) ABSTRACT

A large scale cell harvesting method for a pack-bed culture device by providing cell growing space that is packed with a plurality of porous matrices and/or matrix means. When a cell detaching step at least comprising shaking or spinning the culture chamber is performed, the unoccupied space is large enough for the porous matrices collide to each other or to the culture chamber to generate momentum whereby the cells detach from the porous matrices to harvest the cells.

13 Claims, 6 Drawing Sheets

LARGE SCALE CELL HARVESTING METHOD FOR PACK-BED CULTURE DEVICE

BACKGROUND OF THE INVENTION

1. Field of the Invention

The present invention relates to a large scale cell harvesting method, particularly to a large scale cell harvesting method for pack-bed culture device.

2. Description of the Prior Art

Large-scale cell culture processes have been developed extensively over the years for the growth of bacteria, yeast and molds, all of which typically possess robust cell walls and/or extra cellular materials thus, are more resilient. The structural resilience of these microbial cells is a key factor contributing to the rapid development of highly-efficient cell culture processes for these types of cells. For example, bacterial cells can be grown in very large volumes of liquid medium using vigorous agitation, culture stirring and gas sparging techniques to achieve good aeration during growth while maintaining viable cultures. In contrast, the techniques used for culturing cells such as eukaryotic cells, animal cells, mammalian cells and/or tissue are more difficult and complex because these cells are much more delicate and fragile than microbial cells. These cells can be easily damaged by excessive shear forces that may be resulted from vigorous aeration and agitation required for microbial cultures in conventional bioreactors.

Figure 1:
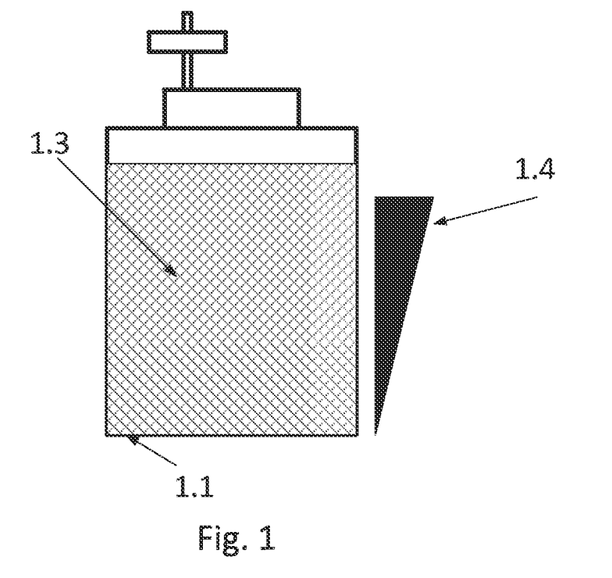
FIG. 1 is a schematic diagram illustrating a packed-bed culture devices of the prior art.

Referring to FIG. 1, which is a schematic diagram illustrating a packed-bed culture devices of the prior art. Packed-bed bioreactor 1.1 contains porous matrices 1.3 for cell growth and protects cells from shear. Due to the matrices provide high surface area, cell density can be higher than the other systems. Usually a density of 5~10×10$^7$ cells/ml matrix can be easily achieved. However, due to the packed-bed functions as a depth filter and is unable to mix after the liquid enter the packed-bed, inoculums are trapped along the flow path through the packed-bed and result a heterogeneous and gradient distribution 1.4 of the cells in the packed-bed.

During culture, nutrient and oxygen also consumed and depleted along with the flow path in the packed-bed so that the oxygen and nutrient is rich at the beginning and is low or depleted at the end of the flow path. All above reasons cause heterogeneous growth of cells in the packed-bed bioreactor and retard the scale up capability in traditional packed-bed bioreactor. However, cell harvest is another important issue in packed-bed bioreactor. Cells are usually difficult to detach from the porous matrices in the packed-bed bioreactor since it is very difficult to apply agitation inside the matrix bed which is essential for cells detaching from the matrices after trypsinization. Therefore, cell source such as inoculums for packed-bed cell culture system usually have to be provided with other cell culture devices, such as tissue culture flasks, roller bottles, cell factory, microcarrier stir tank system, etc. Numbers of cell culture devices are required to collect enough inoculums for seeding in the packed-bed bioreactor. It is tedious and posts the risks to be contaminated during cell harvest process.

To make the scale up of packed bed system become more efficient, a cell harvest system that could harvest cells directly from one packed-bed system and transfer them to another larger scale packed-bed system may make the packed-bed system become a vessel to vessel close transfer system. It may then be able to reduce the risk and labor cost to prepare the inoculums. Therefore, the scale up of packed-bed bioreactor may no longer rely on other cell culture devices.

Another issue when cells were cultured in different culture systems with different culture principle, which might cause the change of cell characteristics. A scale up process using similar culture principle device could alleviate the doubt on altering cell behaviors, which might affect the outcome from the cell culture process.

Therefore, it is now a current goal to develop a method and a packed-bed cell culture device that enables cell harvest from the said device.

SUMMARY OF THE INVENTION

The present invention is directed to providing a cell harvesting method from the packed-bed system so as to scale up easily to any practical production scale.

In one embodiment of the present invention, a large scale cell harvesting method, comprising providing a pack-bed culture device configured with a culture chamber having a cell growing space defined within the culture chamber, wherein the cell growing space is packed with a plurality of porous matrices, a plurality of cells grow on the porous matrices, and a void volume is a space unoccupied by the porous matrices in the cell growing space; performing a first cell detaching step at least comprising shaking or spinning the culture chamber, wherein the void volume is large enough for the porous matrices collide to each other or to the culture chamber to generate momentum whereby the cells detach from the porous matrices; performing a second cell detaching step at least comprising introducing the culture medium and shaking or spinning the culture chamber together with the culture medium; and harvesting the cells.

In another embodiment of the present invention, a large scale cell harvesting method, comprising providing a pack-bed culture device configured with a culture chamber having a cell growing space defined within the culture chamber, wherein the cell growing space is packed with a plurality of matrix means, wherein the matrix means have porous matrices therein and are porous, a plurality of cells grow on the porous matrices, and a void volume is a space unoccupied by the matrix means; performing a first cell detaching step at least comprising shaking or spinning the culture chamber, wherein the void volume is large enough for the matrix means collide to each other or to the culture chamber or flush by liquid to generate momentum whereby the cells detach from the porous matrices; performing a second cell detaching step at least comprising introducing the culture medium and shaking or spinning the culture chamber together with the culture medium; and harvesting the cells.

Other advantages of the present invention will become apparent from the following descriptions taken in conjunction with the accompanying drawings wherein certain embodiments of the present invention are set forth by way of illustration and examples.

BRIEF DESCRIPTION OF THE DRAWINGS

The foregoing aspects and many of the accompanying advantages of this invention will become more readily appreciated as the same becomes better understood by reference to the following detailed descriptions, when taken in conjunction with the accompanying drawings, wherein:

FIGS. 2a and 2b, which are schematic diagrams illustrating a packed-bed culture chamber according to a preferred embodiment of the present invention, where FIG. 2b is the enlarged view of FIG. 2a;

DESCRIPTION OF THE PREFERRED EMBODIMENT

The embodiments of the present invention may be used for harvesting cells from large-scale packed-bed cell culture devices. The present invention is directed to the techniques to culture cells such as eukaryotic cells, animal cells, mammalian cells and/or tissue that are more difficult and complex because these cells are far more delicate and fragile than microbial cells.

Most packed-bed cell culture devices are unable for cell recovery due to the matrix bed are fixed and restrain in a certain space and the container is either glass or metal such as stainless steel, which make the cell harvest impossible. Few commercial packed-bed cell culture devices are capable of cell recovery, such as BelloCell from CESCO Bioengineering Co., Ltd. (www.cescobio.com.tw), where the container is made by flexible plastics. 100 ml matrices are enclosed inside the container. After trypsinization, and by tapping the plastics, the elastic force on the plastic container could be transferred into the matrices and force the cells to be pop out of the matrices for harvest. However, when the same structure is scaled up to one liter or more, the recovery rate will drop dramatically since the force cannot be transferred deeply into the bed.

In order to solve this problem, the matrices are packed with more void volume inside the container and by shaking the matrices themselves with liquid or without liquid or spinning the container with liquid, the force could transfer into each matrix themselves instead of transfer from the wall of the container.

Another issue is when the matrix bed keeps scale up, the matrices themselves work as a filter to re-trap the cells, increased wash steps has to be performed so as to harvest most cells. However, cells tend to re-adhere onto the matrices if the harvest time takes too long. By adding matrix means where matrices are enclosed inside, it could divide the matrices to multiple groups so that cells have room to flow out and reduce the chance to be re-trapped. It will allow increased cell harvest efficiency. Therefore, the present invention is directed to solving or improving the cell recover efficiency from 500 ml up to 100 L matrix volume, in terms of $5 \times 10^9$ cells to $2 \times 10^{12}$ cells. When the matrix volume is lower than 5 L, only increasing the void volume in the matrix bed could enhance the cell recovery rate. When the matrix volume is higher than 5 L, adopting matrix means could more efficiently enhance the cell recovery rate and avoid cells to be re-trapped by the matrices themselves.

Figure 2A:
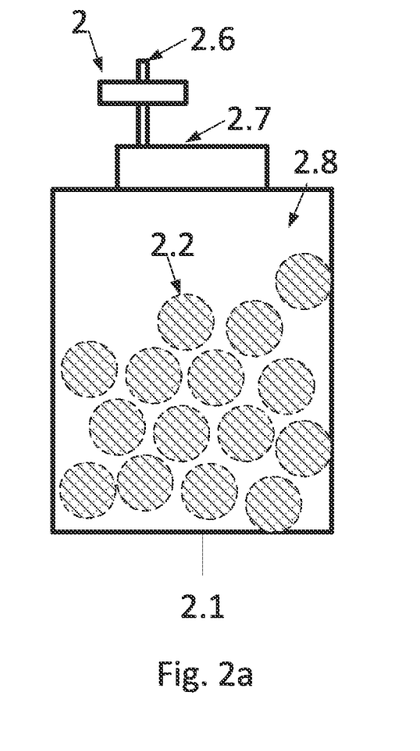
Figure 2B:
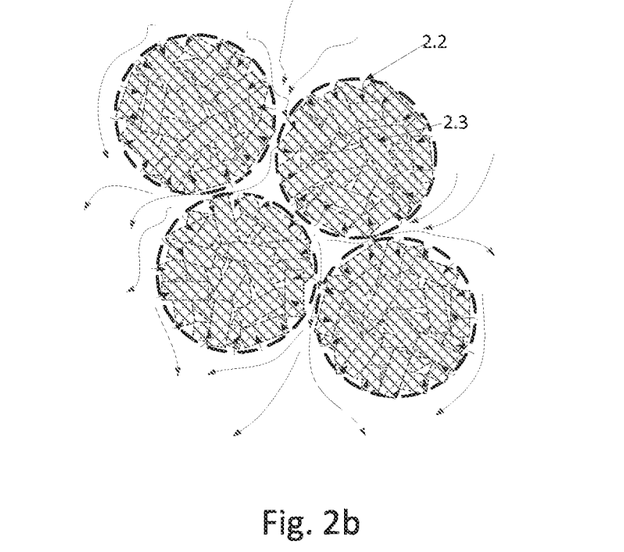

Refer to FIGS. 2a and 2b, which are schematic diagrams illustrating a packed-bed culture chamber according to a preferred embodiment of the present invention, where FIG. 2b is the enlarged view of FIG. 2a. The packed-bed culture chamber 2.1 has openings 2.6 for air inlet and outlet, openings 2.7 on the top of the chamber for introducing cells, culture medium or buffer solution. The openings 2.6 for air inlet and outlet contain an air filter. Porous matrices 2.3/porous matrix means 2.2 are disposed inside the packed-bed culture chamber.

Figure 2C:
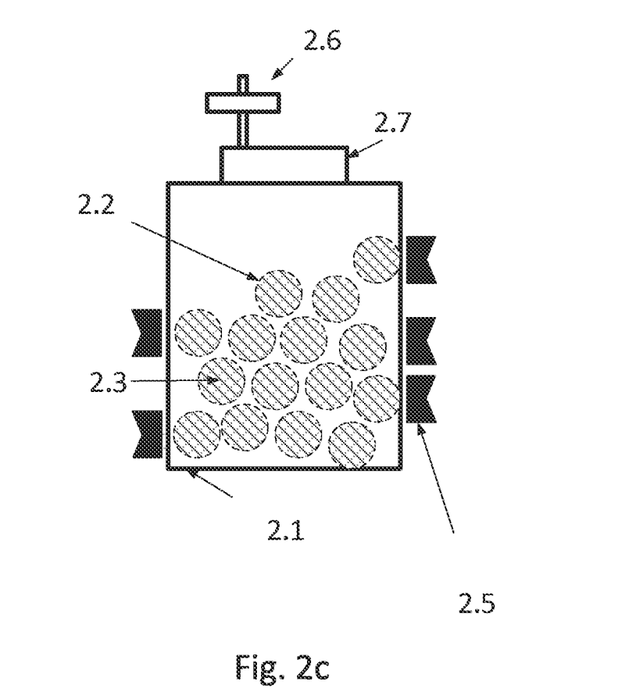
FIG. 2c is a schematic diagram illustrating a fixed-bed cell culture device of the present invention, wherein the distribution gradient profile in the present invention.

Comparing FIG. 1 and FIG. 2c, distribution gradient profile 2.5 in the present invention may be greatly improved compared with conventional packed-bed system where a larger packed-bed causes serious gradient drop along the liquid flow direction and thus limit the scale up capability.

The matrix means 2.2 are made with rigid materials and provided with pores for nutrient and cells to penetrate and exchange freely. The matrix means 2.2 may be provided with different geometry and shape. More preferably, the matrix means 2.2 are in a ball shape, a cylinder shape, a rod shape or an oval shape. More specifically, the matrix means 2.2 are made with rigid materials such as polypropylene, polyethylene, polyethylene tetraphalate (PET), or other biocompatible materials. The matrix means 2.2 could be porous matrices 2.3 themselves, or porous and rigid capsules or cartridges that encapsulate porous matrices 2.3 inside. The size of the matrix means 2.2 could be from 0.5 cm in diameter up to 10 cm in diameter. More preferably, the size of the matrix means 2.2 could be from 0.5 cm up to 5 cm in diameter.

In one embodiment, the matrix means 2.2 consists of two parts that can be assembled to form the matrix means 2.2. The porous matrices 2.3 may be disposed into the parts before assembling so as to be enclosed into the matrix means 2.2.

Porous matrices 2.3 may be enclosed inside the matrix means 2.2. The porous matrices 2.3 are preferably non-woven fibrous matrix with surface treatment to make them hydrophilic. More specifically, the porous matrices 2.3 are macroporous with pore size from 50 um to 200 um and with porosity larger than 70%. More specifically, the porous matrices 2.3 are provided with large amount of surface area for cell entrapping, adhesion, growth, and oxygenation.

The cell growing space is packed with a plurality of porous matrices 2.3/matrix means 2.2 with 33% to 50% void space so as for the porous matrices 2.3/matrix means 2.2 collide to each other or to the culture chamber or flush by the liquid to generate momentum whereby the cells detach from the porous matrices 2.3 and/or the matrix means 2.2.

To be specific, in the case of the cell growing space packed with porous matrices 2.3, the void volume is more than 25% v/v of cell growing space, preferably more than 33% v/v. In the case of the cell growing space packed with matrix means 2.2, the void volume is more than 10% v/v of the cell growing space, preferably more than 33% v/v.

Figure 3:
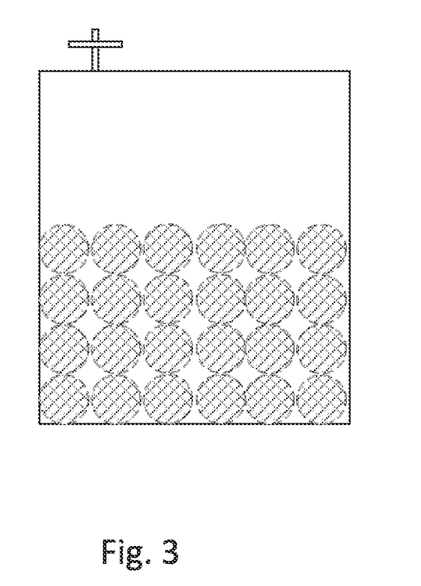
FIG. 3 is a schematic diagram illustrating a fixed-bed cell culture device of the present invention, wherein the culture chamber is packed with a plurality of matrix means that are in a sphere shape.

FIG. 3 is a schematic diagram illustrating a fixed-bed cell culture device of the present invention, wherein the culture chamber is packed with a plurality of matrix means where the porous matrices are embedded inside. The matrix means are in a sphere shape made with rigid materials and provided with pores for nutrient and cells to penetrate and exchange freely.

Figure 4:
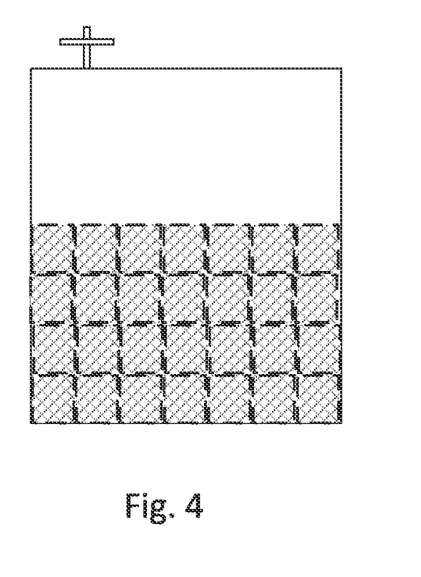
FIG. 4 is a schematic diagram illustrating a fixed-bed cell culture device of the present invention, wherein the culture chamber is packed with a plurality of matrix means that are in a cylinder shape.

FIG. 4 is a schematic diagram illustrating a fixed-bed cell culture device of the present invention, wherein the culture chamber is packed with a plurality of matrix means where the porous matrices are embedded inside. The matrix means are in a cylinder shape made with rigid materials and provided with pores for nutrient and cells to penetrate and exchange freely.

Figure 5:
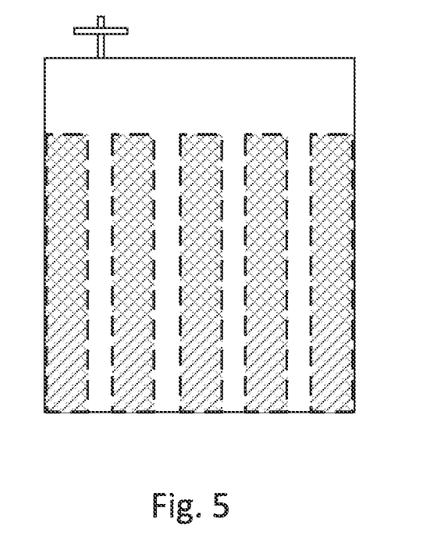
FIG. 5 is a schematic diagram illustrating a fixed-bed cell culture device of the present invention, wherein the culture chamber is packed with a plurality of matrix means that are in a long cylinder shape.

FIG. 5 is a schematic diagram illustrating a fixed-bed cell culture device of the present invention, wherein the culture chamber is packed with a plurality of matrix means where the porous matrices are embedded inside. The matrix means are in a long cylinder shape made with rigid materials and provided with pores for nutrient and cells to penetrate and exchange freely.

Figure 7:
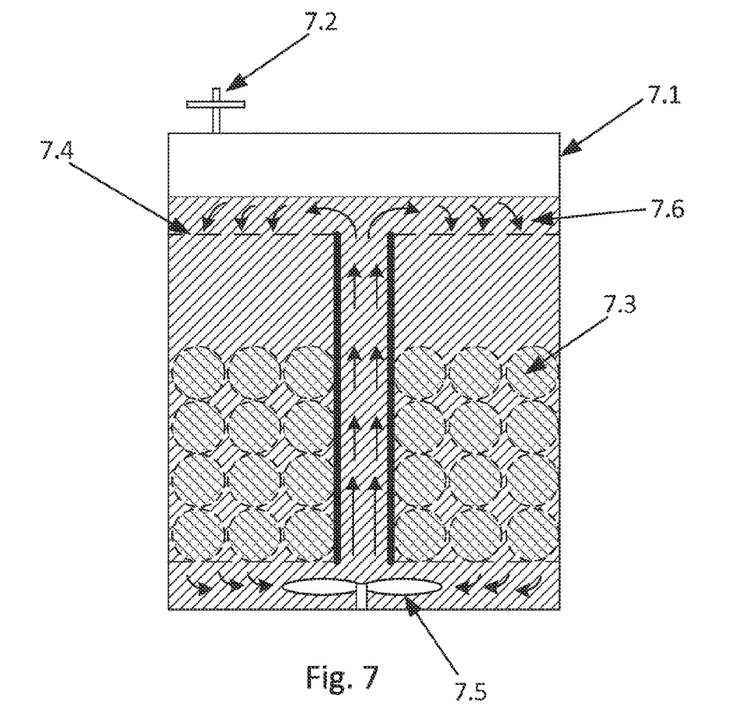
FIG. 7 is a schematic diagram illustrating the cell-cultivating apparatus with inner recirculation according to one preferred embodiment of the present invention.

Refer to FIG. 7, illustrating the cell-cultivating apparatus according to one preferred embodiment of the present invention. The packed-bed system could be an inner recirculation cell culture system, where the culture chamber 7.1 contains an air vent 7.2. The matrix means 7.3 are packed inside the basket 7.4 that could restrain the movement of the matrix means 7.3. Under the culture chamber 7.1 there is a propeller 7.5 for liquid recirculation. The culture medium 7.6 submerges the entire packed-bed and re-circulated as indicated by the arrows inside the culture chamber 7.1

Figure 8:
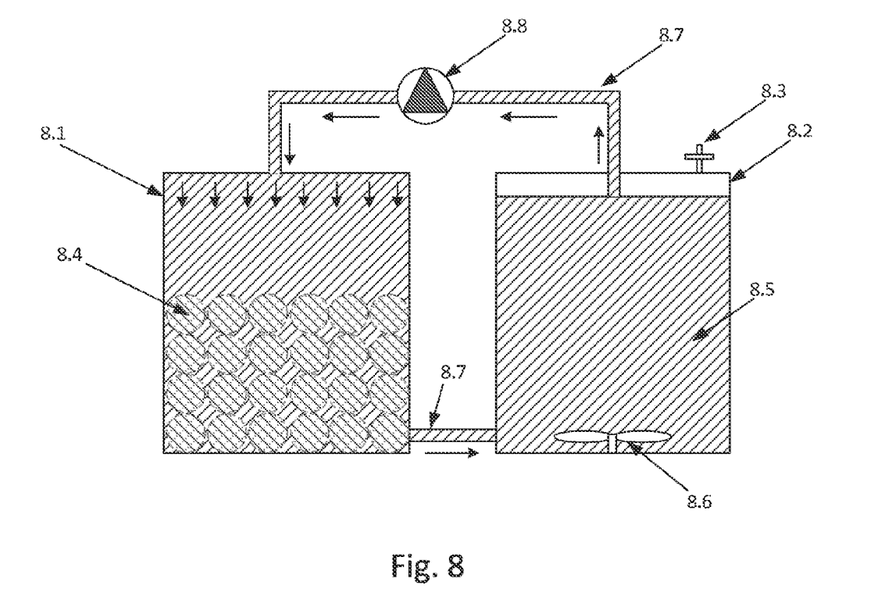
FIG. 8 is a schematic diagram illustrating the cell-cultivating apparatus with outer recirculation according to one preferred embodiment of the present invention.

Referring to FIG. 8, which is a schematic diagram illustrating the cell-cultivating apparatus of one preferred embodiment of the present invention, the packed-bed system could be a cell culture system with outer recirculation, where the culture chamber 8.1 contains the matrix means 8.4. A mixing vessel 8.2 has air vent 8.3 and ports as inlet and outlet 8.7. The culture medium 8.5 is re-circulated between the culture chamber 8.1 and the mixing vessel 8.2 by a peristaltic pump 8.8 or other means. The mixing vessel 8.2 has a propeller 8.6 for homogenizing the culture medium 8.5 during culture. The culture medium 8.5 is re-circulated as indicated by the arrows between the culture chamber 8.1 and mixing vessel 8.2.

Figure 9:
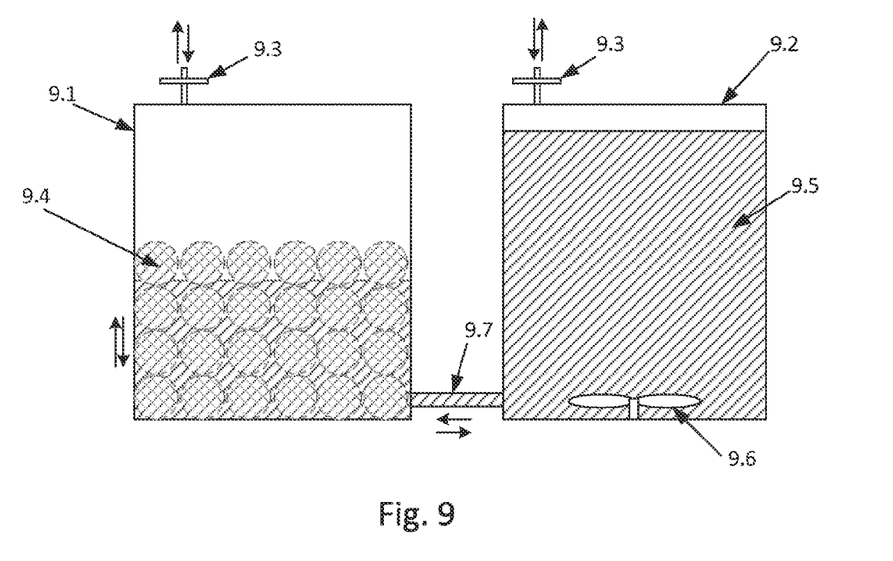
FIG. 9 is a schematic diagram illustrating the cell-cultivating apparatus with intermittent submerge and exposure according to one preferred embodiment of the present invention.

Refer to FIG. 9, which is a schematic diagram illustrating the cell-cultivating apparatus according to a preferred embodiment of the present invention. The packed-bed system could be a dual direction and intermittently submerge and exposure cell culture system, where the culture chamber 9.1 contains an air vent 9.3 and is packed with the matrix means 9.4. A mixing vessel 9.2 has air vent 9.3 and ports 9.7 that connect between the culture chamber 9.1 and the mixing vessel 9.2. The culture medium 9.5 is transferred between the culture chamber 9.1 and the mixing vessel 9.2 by pressure and vacuum or other means. The culture medium 9.5 may submerge the matrix means 9.4 when the culture medium 9.5 flow from the mixing vessel 9.2 to the culture chamber 9.1, or emerge the matrix means 9.4 when the culture medium 9.5 flows from the culture chamber 9.1 to the mixing vessel 9.2. The mixing vessel 9.2 has a propeller 9.6 for homogenizing the culture medium 9.5 during culture. The culture medium 9.5 flow path is indicated by the arrows between the culture chamber 9.1 and mixing vessel 9.2.

Figure 6:
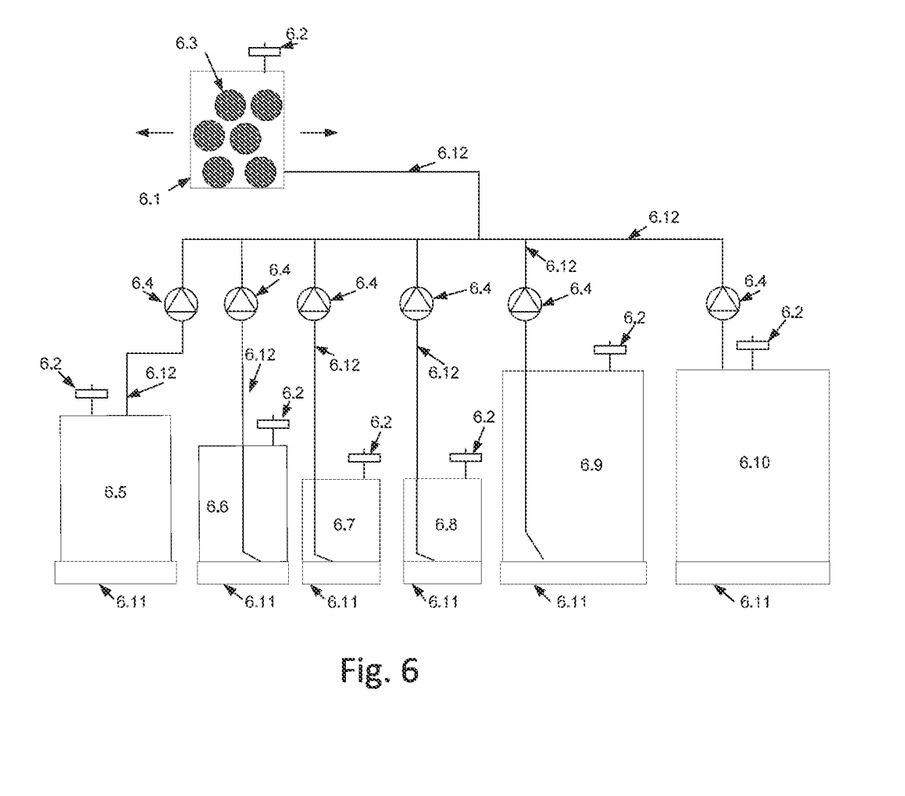
FIG. 6 is a schematic diagram illustrating the cell harvest apparatus of the present invention.

Referring to FIG. 6, which is a schematic diagrams illustrating the cell harvest apparatus of the present invention. The culture chamber 6.1 is provided with the matrix means 6.3 packed inside and optionally an air vent 6.2. After completion of cell culture, the culture chamber 6.1 is connected to a reagent kit that contains necessary reagents and containers for entire cell digestion and collection process. The reagent package may include without limitations to phosphate buffer saline 6.6, trypsin/EDTA 6.7, trypsin inhibitor 6.8, culture medium 6.9, waste container 6.5, and cell harvest container 6.10. Each container has an inlet/outlet 6.12 and optionally an air vent 6.2. Each container is placed on a scale or balance or other means to measure and control the weight. Liquid flow is controlled by peristaltic pump or other driving means 6.4.

Those skilled in the art may well understand the cell harvest procedures such as shaking with liquid or spinning with liquid. The spinning with liquid is rotated clockwise and counter-clockwise intermittently, with the spinning speed ranging from 10 rpm to 500 rpm. The preferable spinning speed ranges from 100 rpm to 300 rpm.

In one embodiment, the cell harvest procedure may be performed as follows:

Step 1. The culture medium inside the culture chamber 6.1 is discarded before connecting with the reagent package by pumping to harvest tanks after the end of cell culture.

Step 2. Connect the culture chamber 6.1 with the reagent package through a tube 6.12.

Step 3. Introduce phosphate buffer saline 6.6 from the vessel 6.6 by peristaltic pump 6.4 or other means into the culture chamber 6.1. The amount of buffer transfer is controlled by the balance 6.11 or other means. The culture chamber 6.1 may then be rotated or shaken gently to rinse the matrix means 6.3 by some means. The phosphate buffer saline may then be transferred from the culture chamber 6.1 to the waste container 6.5 by peristaltic pump or other driving means 6.4. This step could repeat twice or three times.

Step 4. Trypsin/EDTA 6.7 solution is then transferred into the culture chamber 6.1 from the vessel 6.7 by peristaltic pump or other driving means 6.4. The amount of transferred reagent is controlled by the balance 6.11 or other means. The culture chamber 6.1 may then be rotated or shaken gently to rinse the matrix means 6.3 by some means. 5 to 20 minutes incubation may be applied for the trypsin to digest the cells. The trypsin solution may then be transferred from the culture chamber 6.1 to the waste container 6.5 by peristaltic pump or other driving means 6.4. Further incubation may be done after the trypsin solution has been removed from the culture chamber 6.1.

Step 5. Trypsin inhibitor 6.8 is optionally introduced from the vessel 6.8 into the culture chamber 6.1 by peristaltic pump or other driving means 6.4. The amount of reagent transfer may be controlled by means such the balance 6.11 or else. The culture chamber 6.1 may then be rotated or shaken gently to rinse the matrix means 6.3 by some means. The trypsin inhibitor solution may then be transferred from the culture chamber 6.1 to the waste container 6.5 by peristaltic pump or other driving means 6.4.

Step 6. A vigorous shaking and/or spinning with or without liquid may then be applied after the digestion so as to force the matrix means 6.3 to collide with each other or flushed by the mixed liquid. This may help the cells to be dislodged from the porous matrices.

Step 7. Culture medium 6.9 in the vessel 6.9 may then be introduced from the vessel 6.9 into the culture chamber 6.1 by peristaltic pump or other driving means 6.4 if it is shaken without liquid. The amount of transferred medium may be controlled by the balance 6.11 or other means. The culture chamber 6.1 may then be shaken vigorously to rinse the matrix means 6.1 by some means to wash off the cells from the porous matrices. The culture medium solution containing cells may then be transferred from the culture chamber 6.1 to the cell harvest container 6.10 by peristaltic pump or other driving means 6.4.

Repeat Step 6 and Step 7 to collect most of the cells from the matrix means 6.3.

The present invention is further illustrated by the following working examples, which should not be construed as further limiting.

Example 1

A 2 L packed bed culture chamber with porous matrixes means, i.e. 200 g BioNOC II carriers with less than 10% void space. The cell harvest procedure is done by pumping in and rinsing with phosphate buffer saline (PBS) for 3 minutes before discard by pumping out the PBS to a waste container. The step was repeated three times and followed by pumping in 0.25% trypsin/EDTA to submerge the carriers for 10 minutes. The trypsin/EDTA solution was discarded by pumping out to the waste container and cells were then incubated for additional 10 minutes. An up-down shaking with 160 rpm for 1 minute was performed so as to dislodge the cells from the porous matrices. 1.5 L culture medium was pumped in and the culture chamber was spinned clockwise and counterclockwise intermittently at a speed of 100 rpm in order to rinse and wash off the cells. Then the medium was pump out and collected in the harvest container. The shaking, spinning and medium harvest steps were repeated for 5 times. Harvested cell number was counted and compared with initial cell density that was estimated by averaging the cell number from ten pieces of carriers.

TABLE 1

Culture chamber with porous matrixes means with less than 10% void space

| | Total Cell Number | Viability | Recovered Cell Number | Recovery Rate | Acc. Recovery Rate |
|---|---|---|---|---|---|
| Before Harvest | $1.91 \times 10^{10}$ | — | — | — | — |
| PBS Rinse 1 | — | — | — | — | — |
| PBS Rinse 2 | — | — | — | — | — |
| PBS Rinse 3 | — | — | — | — | — |
| Trypsin/EDTA treatment | — | 99.00% | $1.68 \times 10^{7}$ | 0.09% | 0.09% |
| Cell Recovery 1 | — | 98.53% | $6.10 \times 10^{8}$ | 3.19% | 3.28% |
| Cell Recovery 2 | — | 100.00% | $3.88 \times 10^{8}$ | 2.03% | 5.31% |
| Cell Recovery 3 | — | 95.34% | $1.54 \times 10^{8}$ | 0.81% | 6.12% |
| Cell Recovery 4 | — | 98.85% | $2.77 \times 10^{8}$ | 1.45% | 7.57% |
| Cell Recovery 5 | — | 99.10% | $1.31 \times 10^{8}$ | 0.69% | 8.26% |
| End of Harvest | $1.73 \times 10^{10}$ | — | — | — | — |

The overall cell harvest rate in the first example is only 8.26%. Most cells remain in the porous matrices due to less space available during shaking and spinning in order to generate enough momentum to push cells out of the porous matrices.

Example 2

A 2 L packed bed culture chamber with porous matrices, i.e. 110 g BioNOC II carriers that occupied 67% space and with around 33% void space. The cell harvest procedure is done by pumping in and rinsing with phosphate buffer saline (PBS) for 3 minutes before discarded by pumping out the PBS to a waste container. The step was repeated three times and followed by pumping in 0.25% trypsin/EDTA to submerge the carriers for 10 minutes. The trypsin/EDTA solution was discarded by pumping out to the waste container and the cells were then incubated for additional 10 minutes. An up-down shaking with 160 rpm for 1 minute was performed to dislodge the cells from the porous matrices. 1.5 L culture medium was pumped in and the culture chamber was spinned clockwise and counterclockwise intermittently at a speed of 100 rpm in order to rinse and wash off the cells. Then the medium was pump out and collected in the harvest container. The shaking, spinning and medium harvest step was repeated for 5 times. Harvested cell number was counted and compared with initial cell density that was estimated by averaging the cell number from ten pieces of carriers.

TABLE 2

Culture chamber with porous matrixes means with around 33% void space

| | Total Cell Number | Viability | Total Recovered Cells | Recovery Rate | Acc. Recovery Rate |
|---|---|---|---|---|---|
| Initial Cell Number | 1.26E+10 | — | — | — | — |
| PBS Rinse 1 | — | — | 0 | — | — |
| PBS Rinse 2 | — | — | 0 | — | — |
| PBS Rinse 3 | — | — | 0 | — | — |
| Trypsin/EDTA treatment | — | — | 0.00E+00 | 0.00% | 0.0% |
| Cell Recovery 1 | — | 98% | 6.92E+09 | 54.92% | 54.92% |
| Cell Recovery 2 | — | 92% | 2.85E+09 | 22.62% | 77.54% |
| Cell Recovery 3 | — | 85% | 1.05E+09 | 8.33% | 85.87% |
| Cell Recovery 4 | — | 50% | 3.76E+07 | 0.30 | 86.17% |
| Cell Recovery 5 | — | 83% | 6.05E+07 | 0.48% | 86.65% |
| Final Cell Harvest | 1.09E+10 | | | | |

Figure 10:
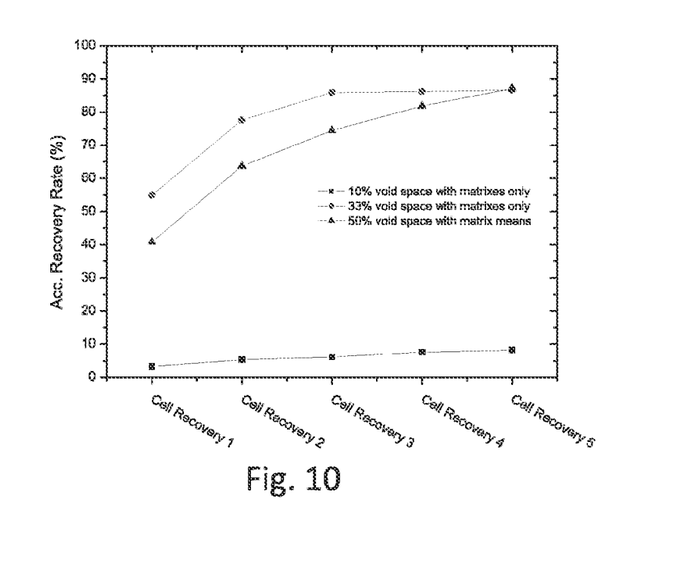
FIG. 10 is a schematic diagram illustrating the cell recovery rate according to one preferred embodiment of the present invention.

Referring to FIG. 10, by increasing the void space and the relative motion between matrices to matrices, and matrices to chamber, or matrices to liquid could be increased dramatically during shaking and spinning. The cell recovery rate could be increased to 86.65% instead of previous example where only 8.26% recovery was reached.

Example 3

A 2 L packed bed culture chamber with porous cylinder matrix means that occupied around 50% of the culture chamber space. Porous matrices, i.e. 110 g BioNOC II carriers are evenly packed inside those porous cylinder matrix means. The cell harvest procedure was done by pumping in and rinsing with phosphate buffer saline (PBS) for 3 minutes before discard by pumping out the PBS to a waste container. The step was repeated three times and followed by pumping in 0.25% trypsin/EDTA to submerge the carriers for 10 minutes. The trypsin/EDTA solution was discarded by pumping out to the waste container and the cells were then incubated for additional 10 minutes. An up-down shaking with 160 rpm for 1 minute was performed to dislodge the cells from the porous matrices. 1.5 L culture medium was pumped in and the culture chamber was spinned clockwise and counterclockwise intermittently at a speed of 100 rpm in order to rinse and wash off the cells. Then the medium was pump out and collected in the harvest container. The shaking, spinning and medium harvest steps were repeated for 5 times. Harvested cell number was counted and compared with initial cell density that was estimated by averaging the cell number from ten pieces of carriers.

TABLE 3

Bed culture chamber with porous matrixes means with around 50% void space

| | Total Cell Number | Viability | Total Recovered Cells | Recovery Rate | Acc. Recovery Rate |
|---|---|---|---|---|---|
| Initial Cell Number | 1.60E+10 | | | | |
| PBS rinse1 | | | | | |
| PBS rinse2 | | | | | |
| PBS rinse3 | | | | | |
| Trypsin/EDTA | | | | | |
| Cell Recovery 1 | | | 6.53E+9 | 40.83% | 40.83% |
| Cell Recovery 2 | | | 3.65E+9 | 22.82% | 63.65% |
| Cell Recovery 3 | | | 1.72E+9 | 10.78% | 74.43% |
| Cell Recovery 4 | | | 1.17E+9 | 7.34% | 81.77% |
| Cell Recovery 5 | | | 8.43E+8 | 5.27% | 87.04% |
| Final Recovery | 1.39E+10 | | | | |

The total recovery rate could reach 87.04% by the void volume of around 50%.

While the invention can be subject to various modifications and alternative forms, a specific example thereof has been shown in the drawings and is herein described in detail. It should be understood, however, that the invention is not to be limited to the particular form disclosed, but on the contrary, the invention is to cover all modifications, equivalents, and alternatives falling within the spirit and scope of the appended claims.

What is claimed is:

1. A large scale cell harvesting method, comprising:
   providing a packed-bed culture device configured with a culture chamber having a cell growing space defined within the culture chamber, wherein
   the cell growing space is packed with a plurality of porous matrices,
   a void volume is a space unoccupied by the porous matrices in the cell growing space, wherein the void volume ranges from 33% v/v to 50% v/v of the cell growing space; and
   growing a plurality of cells on the porous matrices in the cell growing space;
   performing a first cell detaching step at least comprising shaking or spinning the culture chamber, wherein the void volume is large enough for the porous matrices collide with each other or with the culture chamber to generate momentum whereby the cells detach from the porous matrices;
   performing a second cell detaching step at least comprising introducing the culture medium and shaking or spinning the culture chamber together with the culture medium; and
   harvesting the culture medium with the cells.

2. The method as claimed in claim 1, wherein the cells are animal cells.

3. The method as claimed in claim 1, wherein the cells are mammalian cells.

4. The method as claimed in claim 1, wherein the cell detaching step further comprising enzyme digestion, and the enzyme comprises trypsin or EDTA.

5. The method as claimed in claim 1, wherein the spinning with liquid is rotated clockwise and counter-clockwise intermittently.

6. The method as claimed in claim 1, wherein the cell growing space is greater than 500 ml.

7. A large scale cell harvesting method, comprising:
   providing a packed-bed culture device configured with a culture chamber having a cell growing space defined within the culture chamber, wherein
   the cell growing space is packed with a plurality of matrix means, wherein the matrix means are porous and have porous matrices therein,
   a void volume is a space unoccupied by the matrix means in the cell growing space, wherein the void volume ranges from 33% v/v to 50% v/v of the cell growing space; and
   growing a plurality of cells on the porous matrices in the cell growing space;
   performing a first cell detaching step at least comprising shaking or spinning the culture chamber, wherein the void volume is large enough for the matrix means collide with each other or with the culture chamber or flush by liquid to generate momentum whereby the cells detach from the porous matrices;
   performing a second cell detaching step at least comprising introducing the culture medium and shaking or spinning the culture chamber together with the culture medium; and
   harvesting the culture medium with the cells.

8. The method as claimed in claim 7, wherein the cells are animal cells.

9. The method as claimed in claim 7, wherein the cells are mammalian cells.

10. The method as claimed in claim 7, wherein the cell detaching step further comprising enzyme digestion, and the enzyme comprises trypsin or EDTA.

11. The method as claimed in claim 7, wherein the spinning with liquid is rotated clockwise and counter-clockwise intermittently.

12. The method as claimed in claim 7, wherein the matrix means have a ball shape, a cylinder shape, a rod shape or an oval shape.

13. The method as claimed in claim 7, wherein the cell growing space is greater than 500 ml.

* * * * *